(12) United States Patent
Whitney et al.

(10) Patent No.: US 11,707,183 B2
(45) Date of Patent: Jul. 25, 2023

(54) SYSTEMS AND DEVICES FOR ARTICULATION WIRE GUIDANCE

(71) Applicant: Boston Scientific Scimed, Inc., Maple Grove, MN (US)

(72) Inventors: Andrew James Whitney, Douglas, MA (US); Thomas Jeffrey Miller, Issaquah, WA (US); Maria Therese Maillet, Hudson, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

(21) Appl. No.: 16/862,823

(22) Filed: Apr. 30, 2020

(65) Prior Publication Data

US 2020/0345209 A1 Nov. 5, 2020

Related U.S. Application Data (60) Provisional application No. 62/841,290, filed on May 1, 2019.

(51) Int. Cl.
*A61B 1/005* (2006.01)
*A61B 1/00* (2006.01)
(Continued)

(52) U.S. Cl.
CPC .......... *A61B 1/0057* (2013.01); *A61B 1/0052* (2013.01); *A61B 1/00142* (2013.01);
(Continued)

(58) Field of Classification Search
CPC . A61B 1/0057; A61B 1/0052; A61B 1/00098; A61B 2017/00323; A61B 2017/00327; A61M 25/0136; A61M 25/0147; A61M 2025/015; A61M 2025/0161
See application file for complete search history.

(56) References Cited

U.S. PATENT DOCUMENTS 5,606,827 A * 3/1997 Kanou .................. E05F 15/697
49/352
9,931,487 B2 * 4/2018 Quinn ............... A61M 25/0147
(Continued)

FOREIGN PATENT DOCUMENTS

WO 2009140288 A2 11/2009
WO 2015151093 A1 10/2015
WO 2018022402 A1 2/2018

*Primary Examiner* — Nathan J Jenness
*Assistant Examiner* — Thomas Chiang
(74) *Attorney, Agent, or Firm* — Bookoff McAndrews, PLLC (57) ABSTRACT

A steering assembly of a medical device may comprise a handle having a recess and first and second wire guides disposed within the recess. At least one of the first or second wire guides may be keyed to the recess to prevent rotation of the first or second wire guide within the recess. First and second wire segments may be configured to steer a sheath coupled to the steering assembly in first and second directions. The first wire segment may pass through a first gap between the first wire guide and the second wire guide. The second wire segment may pass through a second gap between the first wire guide and the second wire guide. Neither of the first nor the second gap may occupy any overlapping space.

14 Claims, 10 Drawing Sheets

(51) Int. Cl.
  *A61M 25/01* (2006.01)
  *A61M 25/06* (2006.01)
  *A61B 17/00* (2006.01)

(52) U.S. Cl.
  CPC .... *A61M 25/0136* (2013.01); *A61M 25/0147* (2013.01); *A61M 25/0662* (2013.01); *A61B 2017/00323* (2013.01)

(56) References Cited

U.S. PATENT DOCUMENTS

| | | | |
|---|---|---|---|
| 10,405,732 B2* | 9/2019 | Chung | A61B 1/0016 |
| 2004/0193016 A1* | 9/2004 | Root | A61B 1/0052 600/146 |
| 2005/0198937 A1* | 9/2005 | Komiya | F16G 13/16 59/78.1 |
| 2009/0287188 A1* | 11/2009 | Golden | A61M 25/0147 604/528 |
| 2012/0220832 A1* | 8/2012 | Nakade | A61B 1/0057 600/149 |
| 2013/0038930 A1 | 2/2013 | Vent | |
| 2015/0366435 A1 | 12/2015 | Williams | |
| 2017/0051996 A1* | 2/2017 | Evans | F41B 5/10 |

\* cited by examiner

SYSTEMS AND DEVICES FOR ARTICULATION WIRE GUIDANCE

CROSS-REFERENCE TO RELATED APPLICATIONS

This application claims the benefit of priority from U.S. Provisional Application No. 62/841,290, filed on May 1, 2019, which is incorporated by reference herein in its entirety.

TECHNICAL FIELD

The present disclosure relates generally to steering mechanisms for medical devices, including endoscopes. In particular, this disclosure is directed to systems and methods for articulation wire guidance.

BACKGROUND

Handles of endoscopes house multiple components (e.g., steering components) that are kept separate from one another. Placement of such components in handles has involved the use of chains or similar components. Such components increase manufacturing costs by increasing part cost and assembly cost, rendering them unsuitable for use in production of disposable devices. Therefore, a need exists for simple and cost-effective steering assemblies of endoscopes, or other medical devices.

SUMMARY

In one example, steering assembly of a medical device may comprise a handle having a recess and first and second wire guides disposed within the recess. At least one of the first or second wire guides may be keyed to the recess to prevent rotation of the first or second wire guide within the recess. First and second wire segments may be configured to steer a sheath coupled to the steering assembly in first and second directions. The first wire segment may pass through a first gap between the first wire guide and the second wire guide. The second wire segment may pass through a second gap between the first wire guide and the second wire guide. Neither of the first nor the second gap may occupy any overlapping space.

Any example of steering assemblies described herein may have any of the following features. The steering assembly may further include a third wire guide and third and fourth wire segments configured to steer the sheath in third and fourth directions. The third wire segment may pass through a third gap between the second wire guide and the third wire guide. The fourth wire may pass through a fourth gap between the second wire guide and the third wire guide. The first gap and the second gap may be offset from one another. The first and second wire segments may be configured to control left/right movement of the sheath coupled to the steering assembly. The third and fourth wire segments may be configured to control up/down movement of the sheath coupled to the steering assembly. None of the first, second, third or fourth gaps may occupy any overlapping space. The first wire guide may include a first opening for receiving a first axle component. The second wire guide may include a second opening for receiving a second axle component. The third wire guide may include a third opening for receiving a third axle component. Each of the first, second, and third openings may have a different diameter. Each of the first and second wire guides may be keyed to the recess to prevent rotation relative to the recess when disposed therein. Each of the first, second, and third wire guides may be disposed in the recess. Each of the first, second, and third wire guides may be keyed to the recess to prevent rotation relative to the recess when disposed therein. The steering assembly may further include a first pulley coupled to the first and second wire segments. The first pulley may be disposed between the first wire guide and the second wire guide. A second pulley may be coupled to the third and fourth wire segments. The second pulley may be disposed between the second wire guide and the third wire guide. A thickness of the first pulley may maintain the first and the second gaps. A thickness of the second pulley may maintain the third and the fourth gaps. The first wire guide may have first and second offset surfaces that define first portions of the first and the second gaps, respectively. The second wire guide may have third and fourth offset surfaces that define second portions of the first and second gaps, respectively. The first wire guide may have a first step surface extending from the first offset surface to the second offset surface. The second wire guide may have a second step surface extending from the third offset surface to the fourth offset surface. The first and second step surfaces may define third portions of the first and second gaps, respectively.

In a further example, a steering assembly of a medical device may include a handle, first, second, and third wire guides disposed in the handle. At least one of the first, the second, or the third wire guide may be constrained by an axle. First and second wire segments may be configured to control movement of a sheath coupled to the handle in first and second directions, and third and fourth wire segments may be configured to control movement of the sheath in third and fourth directions. The first wire segment may pass through a first gap between the first wire guide and the second wire guide. The second wire segment may pass through a second gap between the first wire guide and the second wire guide. The third wire segment may pass through a third gap between the second wire guide and the third wire guide. The fourth wire segment may pass through a fourth gap between the second wire guide and the third wire guide.

Any example of steering assemblies described herein may have any of the following features. None of the first, the second, the third, or the fourth gaps may occupy any overlapping space. The first gap and the second gap may be offset from one another.

In another example, a steering assembly of a medical device may include first, second, and third wire guides disposed in a handle and a first pulley having first and second wires. The first pulley may be disposed between the first and second wire guides. A second pulley may have third and fourth wires. The second pulley may be disposed between the second and third wire guides. The first, second, and third wire guides and first and second pulleys may be stacked relative to one another to completely contain the first, second, third, and fourth wire segments in separate compartments.

Any example of steering assemblies described herein may further include the handle. The handle may include a recess. Each of the first, second, and third wire guides may be keyed to the recess to prevent rotation relative to the recess when contained therein.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to an operator and the term "distal" means a direction further from an operator. Although endoscopes are referenced herein, reference to endoscopes or endoscopy should not be construed as limiting the possible applications of the disclosed handles and other aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

Handles of endoscopes (e.g., operational portions of endoscopes) may include components that are used by an operator when performing a procedure with the endoscope. For example, a handle of an endoscope may include steering components or assemblies, which may be used to deflect a distal end of a sheath of the endoscope. These steering components or assemblies may include, for example pulleys, drums, and/or wires. Wires of a steering assembly may pass distally from the handle (e.g., handle), into a sheath of an endoscope (e.g., an insertion portion), and through the sheath toward the distal end of the sheath. The wires may be used to deflect the distal end of the sheath in one or more directions. For example, the sheath may include an articulation joint that may be capable of movement in a variety of directions (e.g., 90-360 degrees of movement). Alternatively, the sheath may include any other mechanisms or structures that may be used to achieve movement of the distal end of the sheath. In order to effectively deflect the distal end of the sheath, it may be important to prevent wires of a steering assembly from crossing one another. It also may be important to minimize friction of drums and/or pulleys and to optimize control of drums and/or pulleys. It also may be desirable to utilize components that are relatively inexpensive and/or easier to assemble. Therefore, aspects of the present disclosure are directed to wire guides for positioning and containing wires, drums, and/or pulleys within an endoscope.

Figure 1A:
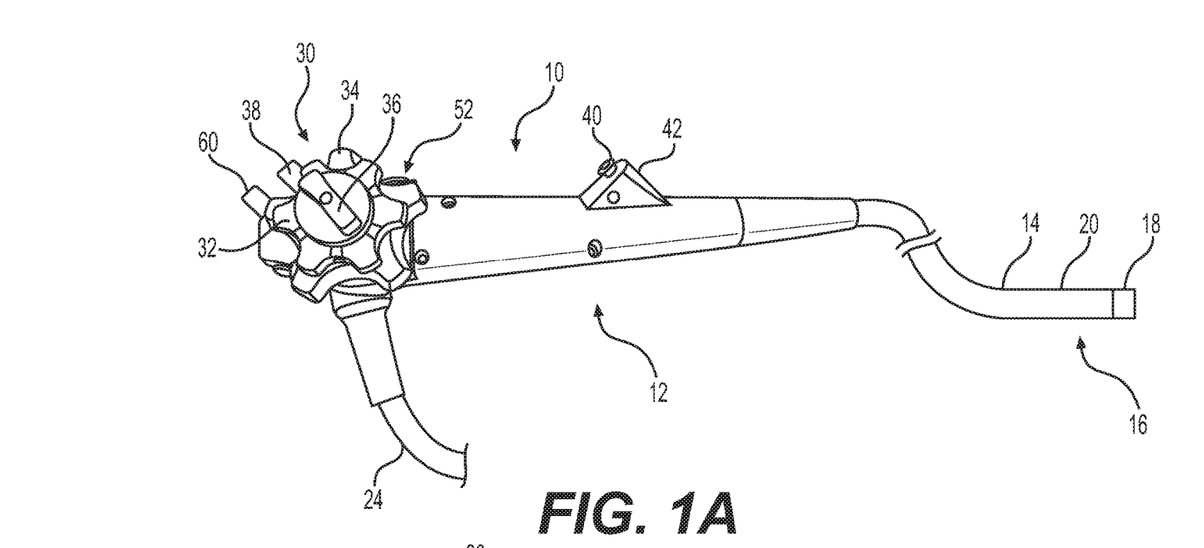
FIG. 1A depicts a perspective view of a medical device.

FIG. 1 depicts a device 10. Device 10 may be an endoscope, duodenoscope, bronchoscope, ureteroscope, colonoscope, catheter, or other type of medical device. Device 10 may include a handle 12. Handle 12 may have any of the features described in the concurrently-filed U.S. Provisional Patent Application entitled "Chambered Handle for a Medical Device," having attorney docket number 06530-0876-00600, the entire disclosure of which is incorporated by reference herein. Device 10 also may include a sheath 14 or other type of tool, which may be inserted into a body lumen of a subject during a medical procedure. A proximal end of sheath 14 may be joined to handle 12. Sheath 14 may include a distal end 16. A distal tip 18 may be the distalmost feature of distal end 16. Distal tip 18 may include a variety of components, such as elevators, air/water/suction openings, working channel opening(s), optical elements (e.g., cameras and/or lenses), lighting devices (e.g., light emitting diodes), etc. An articulation section 20 may be proximal of distal tip 18. Articulation section 20 may include mechanisms configured to facilitate deflection of distal end 16 in one or more directions (e.g., in an up-, down-, left- and/or right-ward directions, perpendicular to a longitudinal axis of device 10).

An umbilicus 24 may extend from handle 12. Umbilicus 24 may be used to connect device 10 to components, such as a controller (for providing, e.g., optical controls including camera, video, light, or other optical controls), an air and/or water supply, and/or a suction supply.

Handle 12 may include a number of components used by an operator to control device 10 before, during, or after a procedure involving device 10. For example, handle 12 may include steering components 30. Steering components 30 may be used to control deflection of articulation section 20. Steering components 30 may be a part of a steering assembly 100 (see FIG. 2), discussed in further detail below. For example, steering components 30 may include two knobs, 32, 34, used for deflecting distal end 16 of sheath 14. For example, one of knobs 32, 34 may be used to deflect distal end 16 of sheath 14 in a left/right direction, and the other of knobs 32, 34 may be used to deflect a distal end 16 of sheath 14 in an up/down direction. Steering components 30 also may include locking mechanisms 36, 38, which may be used to prevent or limit distal end 16 from moving in a left/right and/or up/down direction when in a locking position. For example, locking mechanism 36 may be a knob that is operable to prevent knob 32 from moving, thereby preventing deflection of distal end 16 in a left/right direction. Locking mechanism 38 may be a lever that is operable to prevent knob 34 from moving, thereby preventing deflection of distal end 16 in an up/down direction. Any other suitable feature can be used to prevent movement of knobs 32, 34.

Handle 12 also may include a number of ports and/or valves. For example, handle 12 may include a working channel port 40 that may be used for passing instruments or other devices down a working channel of sheath 14. Working channel port 40 may be housed in a port housing 42. Port 40 may include a valve to prevent leakage. Handle 12 also may include fluidics components, such as valves 52 for providing air, water, and/or suction. Valves 52 may connect to tubing in umbilicus 24, handle 12, and/or sheath 14, such that pressing on valves 52, 5'1 permits the corresponding function. For example, one of valves 52 may be used to provide air and/or water. Another of valves 52 may be used to provide suction and may connect to a working channel extending from working channel port 40.

Handle 12 also may include other components such as elevator lever 60, which may be used to move an elevator (not shown) at distal tip 18 of sheath 14 up and/or down. For example, elevator lever 60 may be included where device 10 is a duodenoscope.

A longitudinal axis of device 10 is an axis extending along handle 12 and sheath 14, and a longitudinal direction is a direction along the longitudinal axis. A radial direction is a direction perpendicular to the longitudinal axis.

Figure 1B:
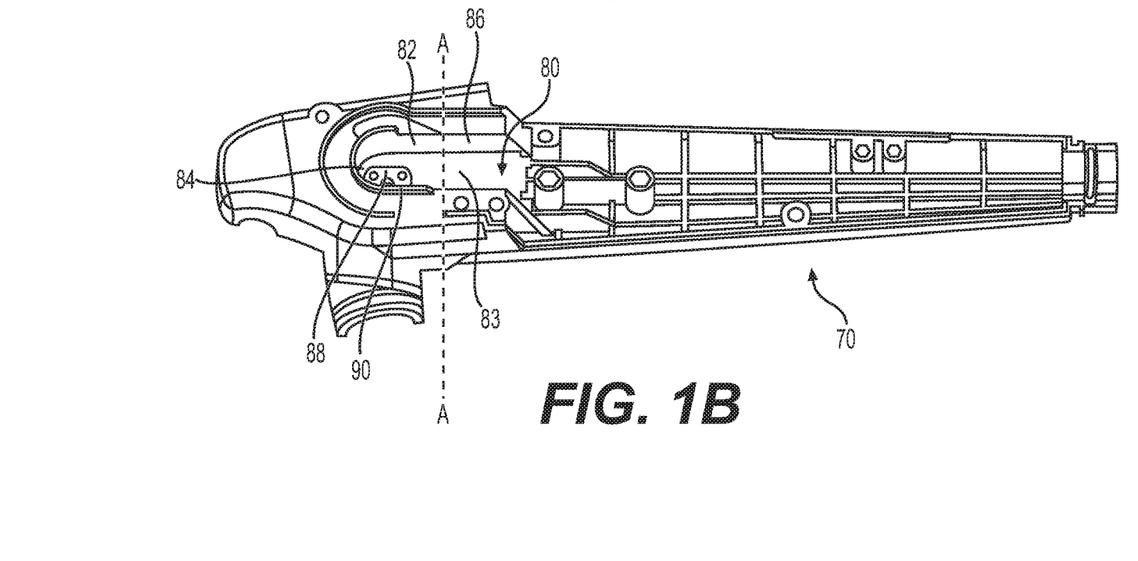
FIG. 1B depicts a perspective view of a handle component of the medical device of FIG. 1A.

FIG. 1B shows a body 70 of handle 12, without many of the components used for operation of device 10 installed. Body 70 may include a first recess 80. First recess 80 may have walls 82 surrounding some but not all of first recess 80. First recess 80 may be open at a distal end of first recess 80 and at an external side of body 70. First recess 80 may have a rounded proximalmost side or end 84, which may be semicircular or u-shaped. An internal surface (which may be a bottom surface) 83 of first recess 80 may extend from the open distal end to rounded proximalmost end 84, opposite the open external side. Internal surface 83 may be parallel or approximately parallel to a longitudinal axis of body 70 and/or device 10. First recess 80 may have two lateral surfaces 86 extending between the open distal end and the rounded proximalmost side 84. As used herein, an outward direction is a direction extending from internal surface 83 through the open external side of first recess 80, and an inward direction is the opposite direction. Alternatively, first recess 80 may have walls 82 surrounding other subsets of first recess 80. First recess 80 may include a second recess 88, which may be more deeply recessed than first recess 80 relative to the open external side of first recess 80. For example, second recess 88 may be recessed from internal surface 83.

Walls 82 may have a uniform height or may have a varying height measured along a radial direction of main body 70. A ridge 90 may extend around a portion of a perimeter of first recess 80. For example, ridge 90 may extend around a curved, proximalmost side 84 of first recess 80. Ridge 90 also may extend along part of a lateral surface 86 of first recess 80. For example, ridge 90 may extend along a part of a straight side of first recess 80 that is closer to umbilicus 24.

Figure 2:
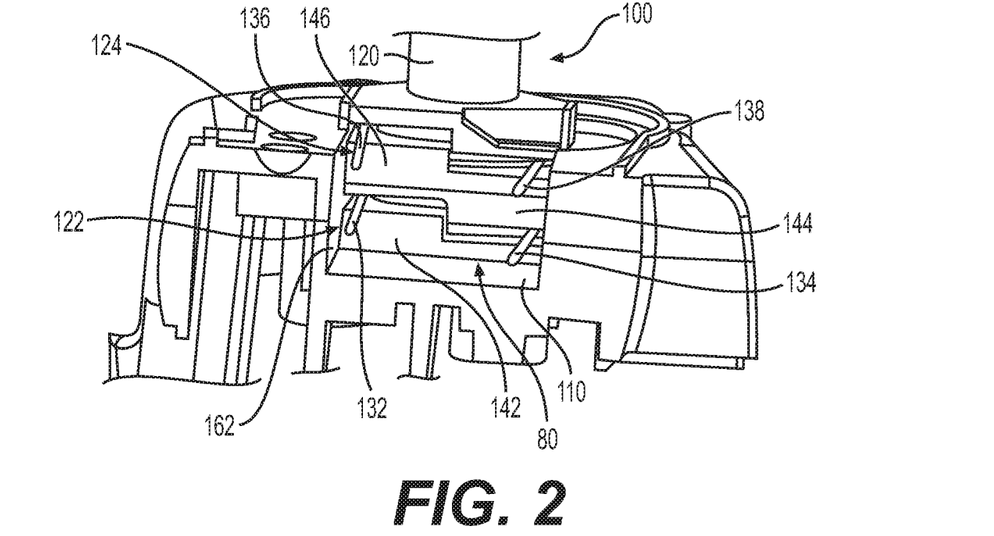
FIG. 2 shows a cross-sectional view of a portion of the medical device of FIG. 1A.

As shown in FIG. 2, a cable steering assembly 100 may be fit within, disposed upon, or otherwise attached to handle 12. For example, cable steering assembly 100 may be received in first recess 80. Cable steering assembly 100 may include an axle assembly 120, which may include one or more axles, as discussed in further detail below. Cable steering assembly also may include two pairs of wires 122, 124 for effecting deflection of a distal end 16 of sheath 14. Pairs of wires 122, 124 may each include two separate wires, which may each terminate in a ferrule and be affixed to a slot in a pulley (as discussed in further detail below). Alternatively, each pair of wires 122, 124 may include a pair of wire segments formed from one single wire looped around a spool or pulley. First pair of wires 122 may control movement in one direction, such as in a left/right direction. Second pair of wires 124 may control movement in another direction, such as in an up/down direction. The configuration of pairs of wires 122, 124 is merely exemplary. Alternative structures may be used, and pairs of wires 122, 124 may be omitted in favor of other types of mechanisms for deflecting distal end 16 of sheath 14.

First pair of wires 122 may include a first wire (or wire segment) 132 and a second wire (or wire segment) 134. Moving first wire 132 proximally may cause distal end 16 of sheath 14 to deflect in a first direction (e.g., a rightward direction). Moving second wire 134 proximally may cause distal end 16 of sheath 14 to deflect in a second direction that is opposite the first direction (e.g., a leftward direction). Proximal movement of first wire 132 may accompany distal movement of second wire 134. Proximal movement of second wire 134 may accompany distal movement of first wire 132. First wire 132 and second wire 134 may be moved either proximally or distally by, for example, turning knob 32 or by activating an alternative mechanism, such as another component of steering components 30. Turning knob 32 in a first direction may cause deflection in a first direction, and turning knob 32 in a second direction may cause deflection in a second direction.

Second pair of wires 124 may include a third wire 136 and a fourth wire 138. Moving third wire 136 proximally may cause a distal end 16 of sheath 14 to deflect in a third direction (e.g., a downward direction). Moving fourth wire 138 proximally may cause a distal end 16 of sheath 14 to deflect in a fourth direction that is opposite of the third direction (e.g., an upward direction). Proximal movement of third wire 136 may accompany distal movement of fourth wire 138. Proximal movement of fourth wire 138 may accompany distal movement of third wire 136. Third wire 136 and fourth wire 138 may be moved either proximally or distally by, for example, turning knob 34 or by activating an alternative mechanism, such as another component of steering components 30. Turning knob 34 in a first direction may cause deflection in a third direction, and turning knob 34 in a second direction may cause deflection in a fourth direction.

As shown in FIG. 2, first wire 132 and second wire 134 may be spaced apart from one another and maintained substantially parallel to one another in first recess 80 of handle 12 by a first wire guide 142 and/or a second wire guide 144. Interaction between first wire guide 142 and second wire guide 144, as discussed in further detail below, may facilitate spacing of first wire 132 and second wire 134 from one another. Third wire 136 and fourth wire 138 may be spaced apart from one another and maintained substantially parallel to one another in first recess 80 of handle 12 by a second wire guide 144 and/or a third wire guide 146. Interaction between second wire guide 144 and third wire guide 146, as discussed in further detail below, may facilitate spacing of third wire 136 and fourth wire 138 from one another. As also shown in FIG. 2, second wire guide 144 may serve to space first pair of wires 122 from second pair of wires 124. Second wire guide 144 may keep first wire 132 substantially parallel to third wire 136 in first recess 80. Second wire guide 144 also may keep second wire 134 substantially parallel to fourth wire 138 in first recess 80.

Wire guides 142, 144, 146 may keep wires 132, 134, 136, and 138 apart from one another. For example, wire guides 142, 144, 146 may be arranged to space apart wires 132, 134, 136, and 138 from one another and maintain their positions on their respective pulleys. In other words, wire guides 142, 144, and 146 may form barriers that prevent wires 132, 134, 136, and 138 from contacting one another. This may help avoid crossing of wires 132, 134, 136, and 138, which may interfere with steering distal end 16 of sheath 14. In addition, this may help ensure wires are maintained in appropriate positions with respect to the pulleys.

Figure 3:
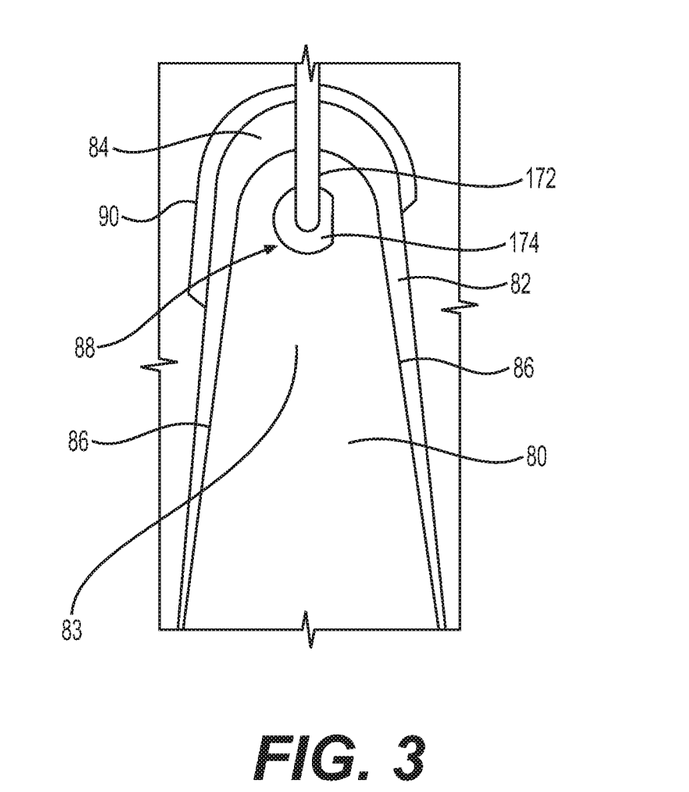
FIG. 3 shows a perspective view of the partially-assembled state of the medical device of FIG. 1A.

FIG. 3 shows first recess 80 and ridge 90, isolated from other components of handle 12. An axle 172 of steering components 30 may be fixed to a body of handle 12. For example, axle 172 may be fixed to a body of handle 12 using a washer or flange 174. Flange 174 may have a complementary shape to second recess 88 so that there is a keyed relationship between flange 174 and second recess 88. A keying relationship between flange 174 and second recess 88 may minimize or entirely prevent rotation of flange 174 within second recess 88.

Figure 4A:
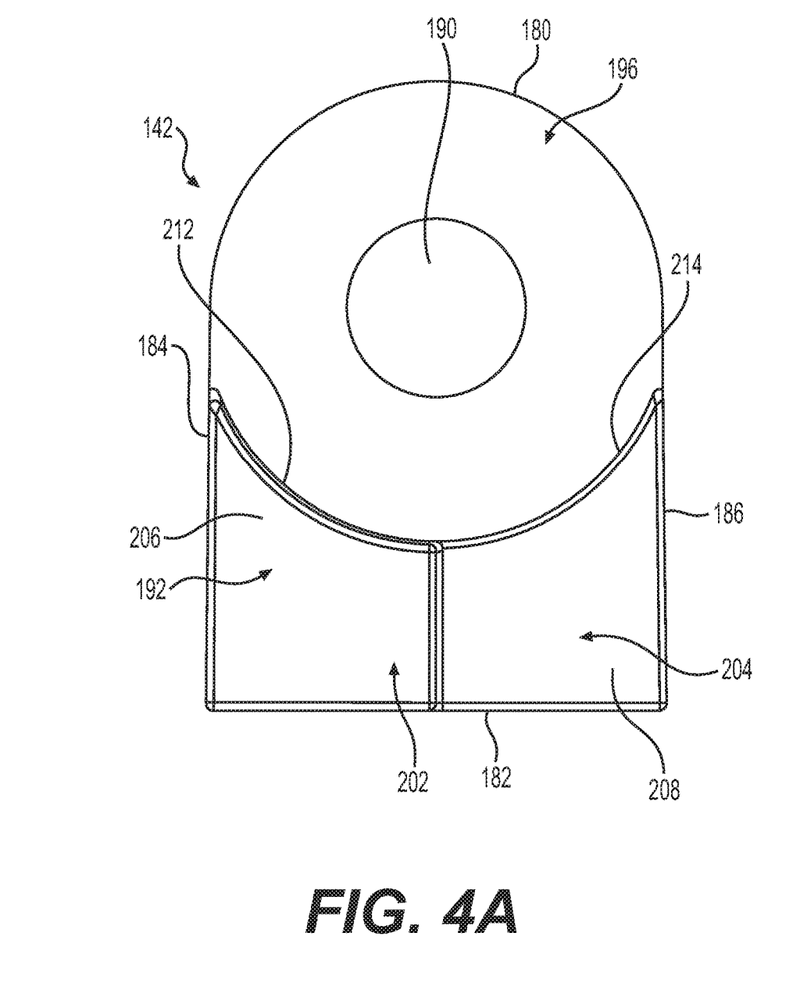
FIGS. 4A-4D show views of a first wire guide.
Figure 4B:
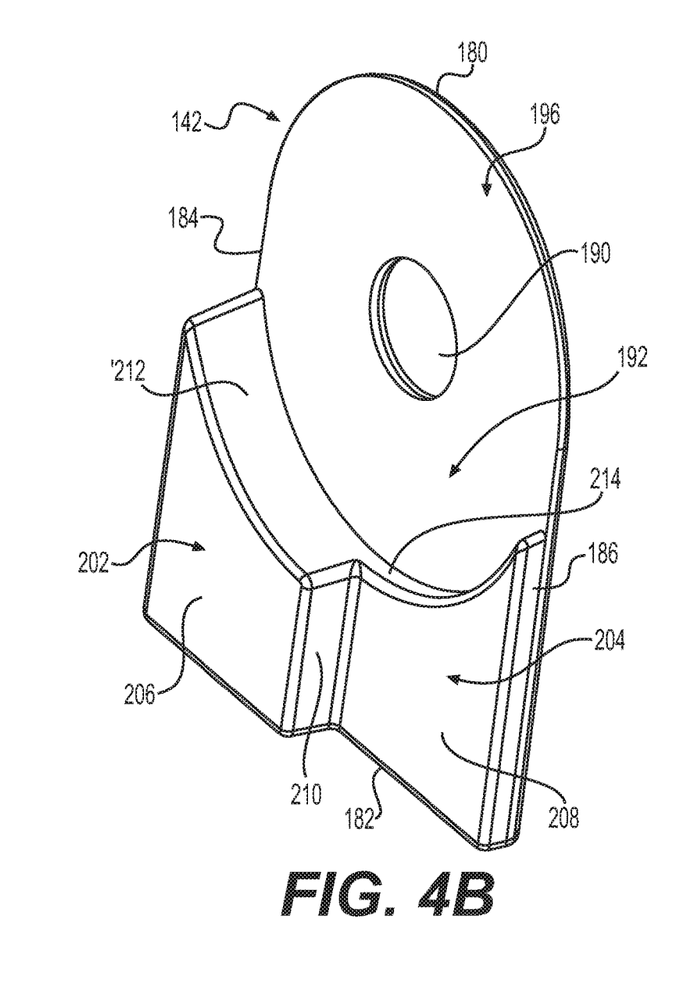
Figure 4C:
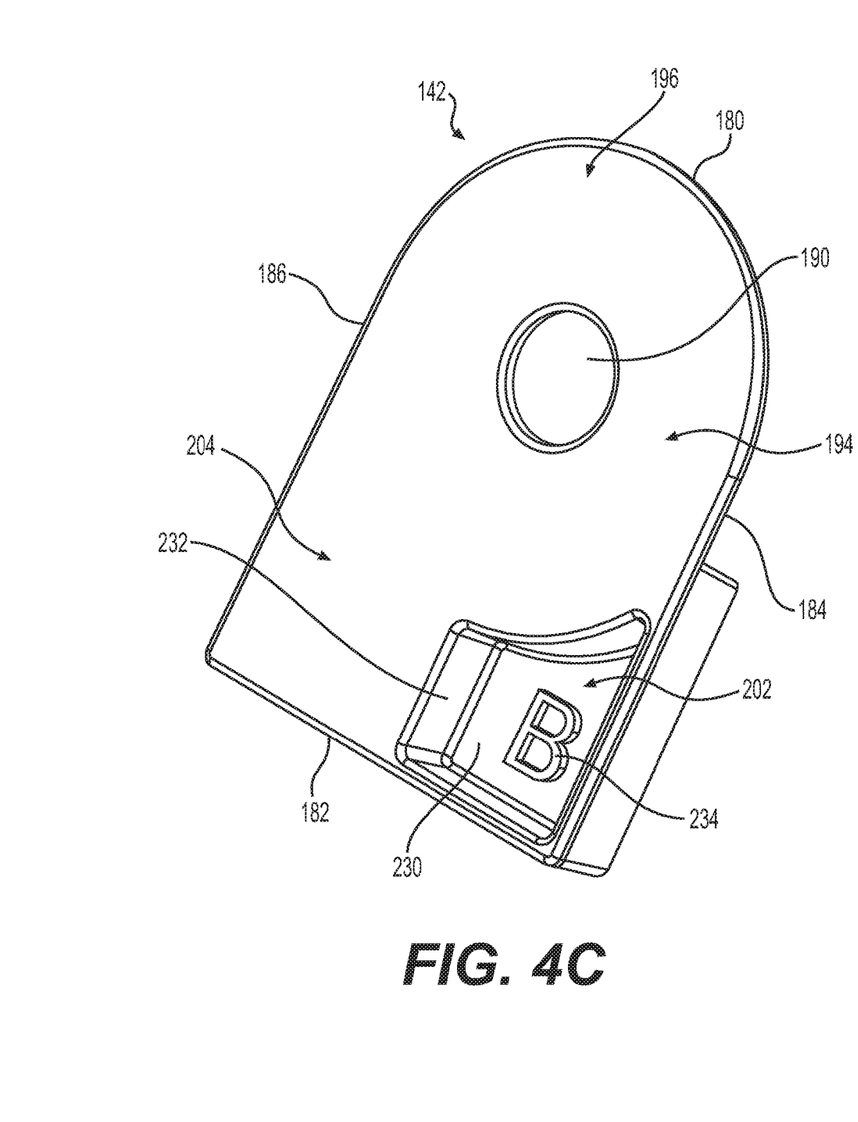
Figure 4D:
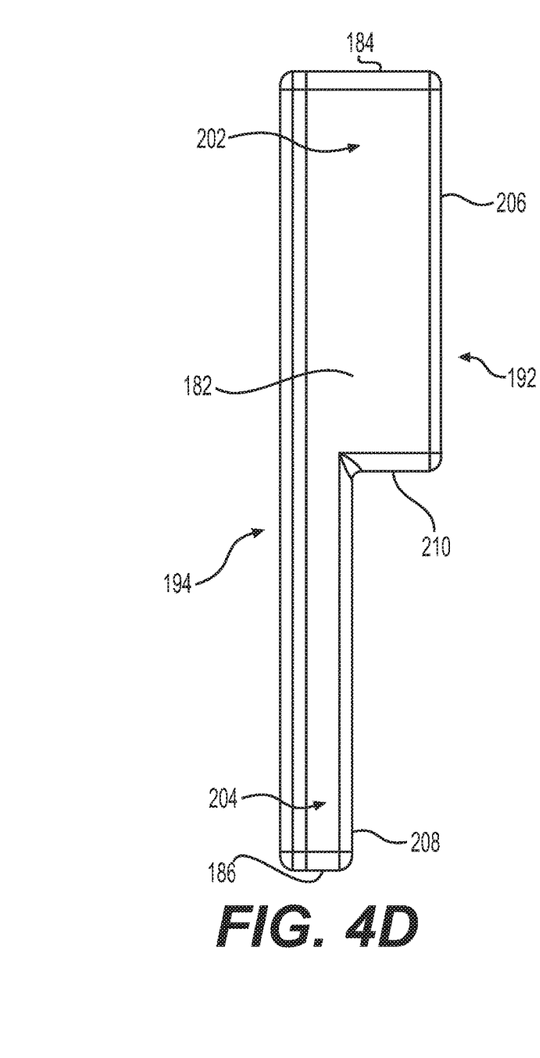
Figure 5A:
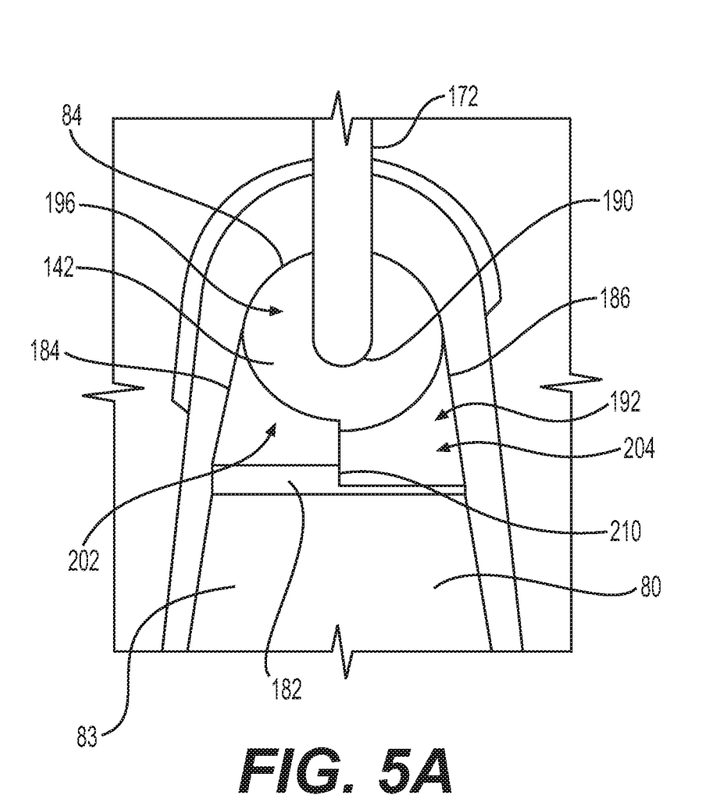
FIGS. 5A-5B show perspective views of handle components of the partially-assembled state of the medical device of FIG. 1A.
Figure 5B:
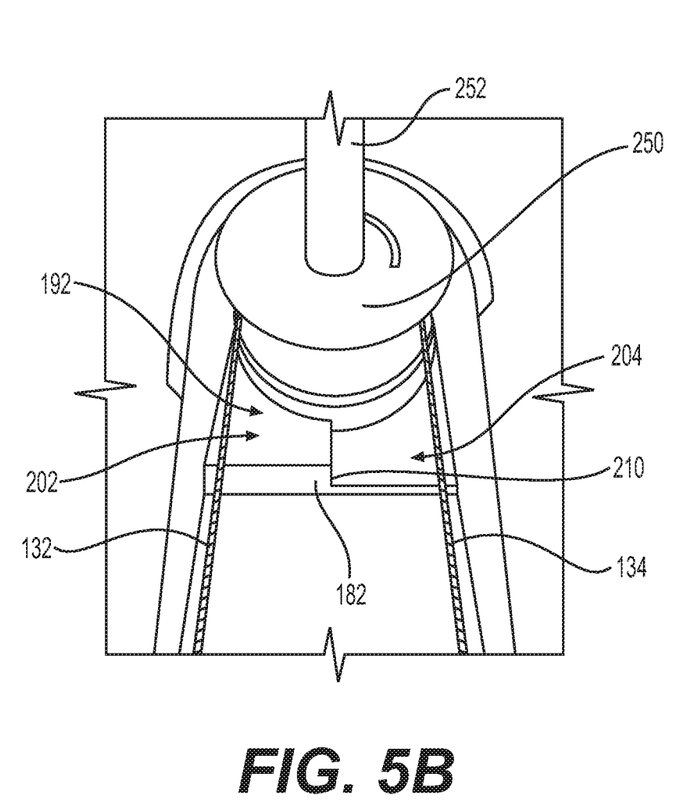

FIGS. 4A-4D show aspects of first wire guide 142. FIG. 4A shows a front view of first wire guide 142. FIGS. 4B and 4C show perspective views of first wire guide 142. FIG. 4D shows a bottom view of first wire guide 142. FIGS. 5A and 5B show first wire guide 142 positioned in first recess 80. First wire guide 142 may have a perimeter that complements a shape of first recess 80. For example, as shown in FIG. 4A, a proximalmost portion or side 180 of first wire guide 142 may have a rounded shape. A radius of curvature of proximalmost side 180 of first wire guide 142 may be the same as or slightly less than a radius of curvature of proximalmost side 84 of first recess 80. First wire guide 142 may have a keyed relationship with first recess 80 to minimize or prevent rotation of first wire guide 142 relative to first recess 80. As also shown in FIG. 4A, first wire guide may include a distalmost side 182, which may be straight. First wire guide 142 also may include a first lateral side 184 and a second lateral side 186, each of which may extend between proximalmost side 180 and distalmost side 182. Shapes of first and second lateral sides 184, 186 may be such that they mate with walls 86 of first recess 80. For example, first and second lateral sides 184, 186 may be straight. A shape of first wire guide 142 may assist in quick installation of first wire guide 142, because wire guide 142 is not symmetrical and should be installed so that curved proximalmost side 180 of first wire guide 142 is adjacent to proximalmost side 84 of first recess 80.

First wire guide 142 may have an opening 190. Opening 190 may have a rounded shape (e.g., a circular shape). Opening 190 may be sized so as to have approximately the same diameter as axle 172 or a diameter that is slightly larger than a diameter of axle 172. Opening 190 may be positioned closer to proximalmost side 184 than distalmost side 182. Openings in any of the wire guides disclosed herein may be constrained via interactions between openings of the wire guides and axle 172 (or other axles or shafts).

First wire guide 142 may have a first side 192 and a second side 194, each of which may extend from proximalmost side 180 to distalmost side 182. FIG. 4B, in particular, shows aspects of first side 192. FIG. 4C, in particular, shows aspects of second side 194.

First wire guide 142 may have a proximal portion 196. Proximal portion 196 may have a washer-type shape. For example, proximal portion 196 may include opening 190 and may include a portion of first wire guide 142 that is concentric to opening 190.

First wire guide 142 may also have a first distal portion 202 and a second distal portion 204. First distal portion 202 may extend from first lateral side 184 toward second lateral side 186, but may terminate prior to second lateral side 186. Second distal portion may 204 may extend from second lateral side 186 toward first lateral side 184, but may terminate prior to first lateral side 184. For example, each of first distal portion 202 and second distal portion 204 may terminate halfway or approximately halfway between first lateral side 184 and second lateral side 186, although other dimensions are contemplated. Each of first distal portion 202 and second distal portion 204 may have a thickness that is greater than a thickness of proximal portion 196. In other words, a distance between first side 192 and second side 194 may be greater at each of first distal portion 202 and second distal portion 204 than at proximal portion 196. As shown in FIG. 4B, first distal portion 202 and second distal portion 204 may be raised or protruding with respect to proximal portion 196 on first side 192.

With particular reference to FIG. 4B, on first side 192, first distal portion 202 may be more raised relative to proximal portion 196 than second distal portion 204. First distal portion 202 may be thicker than second distal portion 204. In other words, a distance between first side 192 and second side 194 may be greater at first distal portion 202 than at second distal portion 204.

FIG. 4D shows a bottom view of first wire guide 142, so that distalmost side 182 is shown. Along distalmost side 182, second side 194 may be flat. Along distalmost side 182, first side 192 may be staggered so that there is a first flat portion 206 (along first distal portion 202) and a second flat portion 208 (along second distal portion 204), with a step 210 between first flat portion 206 and second flat portion 208. First flat portion 206 and second flat portion 208 may be offset from one another. First flat portion 206 and second flat portion 208 may be substantially parallel to one another. Step 210 may form a boundary between first flat portion 206 and second flat portion 208. Step 210 may be substantially perpendicular to both first flat portion 206 and second flat portion 208.

On first side 192, first distal portion 202 may have a proximal edge 212, and second distal portion 204 may have a proximal edge 214. Proximal edges 212, 214 of first and second distal portions 202, 204, respectively, may be adjacent to proximal portion 196. Proximal edges 212, 214 may have a rounded, concave shape that each may be segments of a same circle. Proximal edges 212, 214 may have a same or similar shape when first side 192 is viewed head-on, as shown in FIG. 4A, although proximal edges 212, 214 may have different thicknesses. For example, proximal edge 212 may be thicker than proximal edge 214. A difference in thickness between proximal edge 212 and proximal edge 214 may correspond to a difference in thickness between first distal portion 202 and second distal portion 204.

With particular reference to FIG. 4C, first distal portion 202 may be hollow so that first distal portion 202 includes a recess 230 on second side 194. Recess 230 may have interior walls 232 that follow the contours of first distal portion 202. The fact that first distal portion 202 may be hollow may result in decreased manufacturing costs and mass of first wire guide 142. Recess 230 may maintain a constant thickness of walls of first wire guide 142, facilitating molding of first wire guide 142 or other manufacturing techniques of first wire guide 142. Alternatively, recess 230 may have any of the properties of recess 430, discussed below with respect to third wire guide 146. Recess 230 or another portion of first wire guide 142 also may include an indicator 234. Indicator 234 may indicate, for example, an orientation of wire guide 142 within handle 12. For example, indicator 234 may be a "B," e.g., a first symbol, or any other suitable symbol, indicating that first wire guide 142 is the bottom wire guide that will be adjacent to internal surface 83 of recess 80. Alternatively, other indicators may be used.

FIG. 5A shows first wire guide 142 placed in recess 80. FIG. 5B shows a first pulley 250 installed adjacent to first side 192 of first wire guide 142 (above first wire guide 142). As used herein, the term "above" or "on top of" indicates an outward direction, toward the open external side of recess 80. The term "below" or "underneath" indicates an inward direction, toward internal surface 83. First wire guide 142 may be positioned in first recess 80 so that second side 194 of first wire guide 142 is adjacent to internal surface 83 of first recess 80. First side 192 may face the open external side of first recess 80. Axle 172 may extend through opening 190. For example, first wire guide 142 may be positioned so that axle 172 is aligned with opening 190, and then first wire guide 142 may be advanced along axle 172 until it rests on internal surface 83 of first recess 80. First pulley 250 may abut first wire guide 142, or there may be a gap between first pulley 250 and first wire guide 142. First pulley 250 may have a spool shape. First pulley 250 may have an outer diameter such that first pulley 250 aligns with proximal portion 196 of first wire guide 144 and abuts proximal edges 212, 214. For example, a diameter of proximal portion 196 may be substantially equal to a diameter of first pulley 250. First pair of wires 122 (first wire 132 and second wire 134) may be wrapped around first pulley 250. As discussed above, first pair of wires 122 may be one continuous wire or may include separate wires. First pulley 250 may be attached to a first pulley axle 252, which may be a component of axle assembly 120, and which may be coaxial with axle 172. First pulley axle 252 may be fixed relative to first pulley 250 so that rotation of first pulley axle 252 causes rotation of first pulley 250. First pulley axle 252 may be operatively connected to knob 32 for causing rotation of first pulley axle 252. First wire 132 may pass along first flat surface 206 of first distal portion 202. Second wire 134 may pass along second flat surface 208 of second distal portion 204.

Figure 6A:
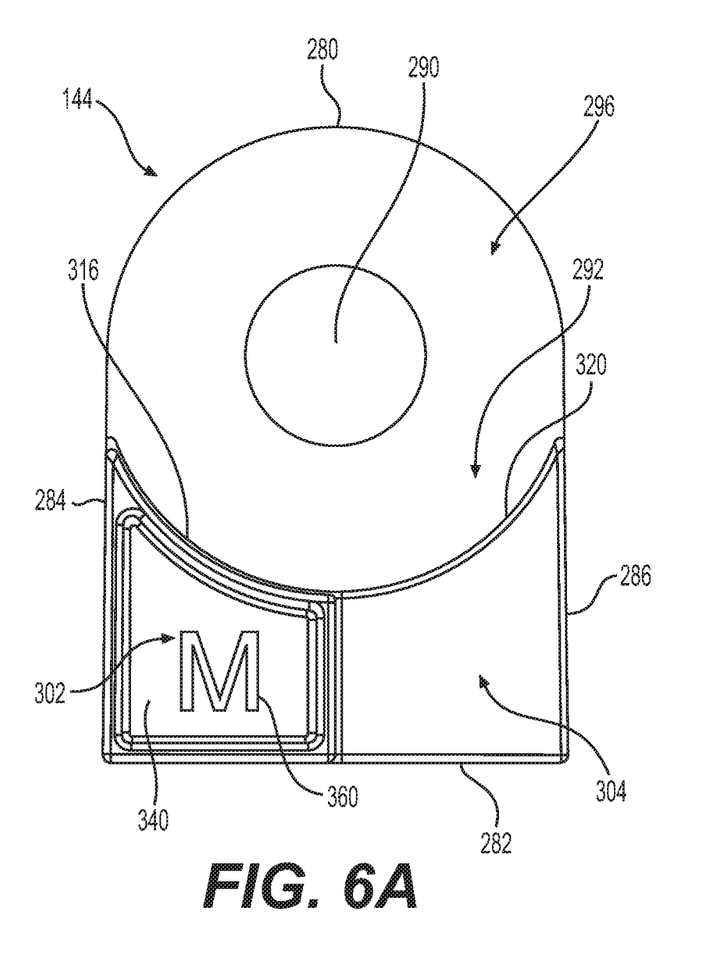
FIGS. 6A-6D show views of a second wire guide.

FIGS. 6A-6D show aspects of second wire guide 144. FIGS. 7A-7B show second wire guide 144 installed in first recess 80 of handle 12. A perimeter shape of second wire guide 144 may have any of the features of a perimeter shape of first wire guide 142, discussed above. For example, second wire guide 144 may have a same perimeter shape as first wire guide 142. For example, as discussed above with respect to first wire guide 142, second wire guide 144 may have a perimeter shape that complements a shape of first recess 80.

Second wire guide 144 may include a proximalmost side 280, which may be curved, and a distalmost side 282, which may be straight. Second wire guide 144 also may include a first lateral side 284 and a second lateral side 286, each of which may extend between proximalmost side 280 and distalmost side 282. Shapes of first and second lateral sides 284, 286 may be such that they mate with lateral surfaces 86 of first recess 80. For example, first and second lateral sides 284, 286 may be straight. A shape of first wire guide 144 may assist in quick installation of second wire guide 144.

Second wire guide 144 may have an opening 290. Opening 290 may have a rounded shape (e.g., a circular shape). Opening 290 may be sized so as to have approximately the same diameter as first pulley axle 252. Opening 290 may have a diameter that is slightly larger than a diameter of first pulley axle 252. Opening 290 may be positioned closer to proximalmost side 280 than to distalmost side 282. Opening 290 may have a larger diameter than opening 190 because first pulley axle 252 may have a larger diameter than axle 172.

Second wire guide 144 may have a first side 292 (see FIGS. 6A, 6B) and a second side 294 (see FIG. 6C), each of which may extend from proximalmost end 280 to distalmost end 282. First and second sides 292, 294 may be the same as one another when viewed head-on. Thus, although FIG. 6A specifically depicts first side 292, first side 292 may be the same as second side 294.

Second wire guide 144 may have a proximal portion 296. Proximal portion 296 may have a washer-type shape. For example, proximal portion 296 may include opening 290 and may include a portion of second wire guide 144 that is concentric to opening 290.

Second wire guide 144 may also have a first distal portion 302 and a second distal portion 304. First distal portion 302 may extend from first lateral side 284 toward second lateral side 286, but may terminate prior to second lateral side 286. Second distal portion 304 may extend from second lateral side 286 toward first lateral side 284, but may terminate prior to first lateral side 284. For example, each of first distal portion 302 and second distal portion 304 may terminate halfway or approximately halfway between first lateral side 284 and second lateral side 286. Each of first distal portion 302 and second distal portion 304 may have a thickness that is greater than a thickness of proximal portion 296. In other words, a distance between first side 292 and second side 294 may be greater at each of first distal portion 302 and second distal portion 304 than at proximal portion 296. As shown in FIG. 4B, first distal portion 302 and second distal portion 304 may be raised or protruding with respect to proximal portion 296 on first side 292 and on second side 294.

Figure 6B:
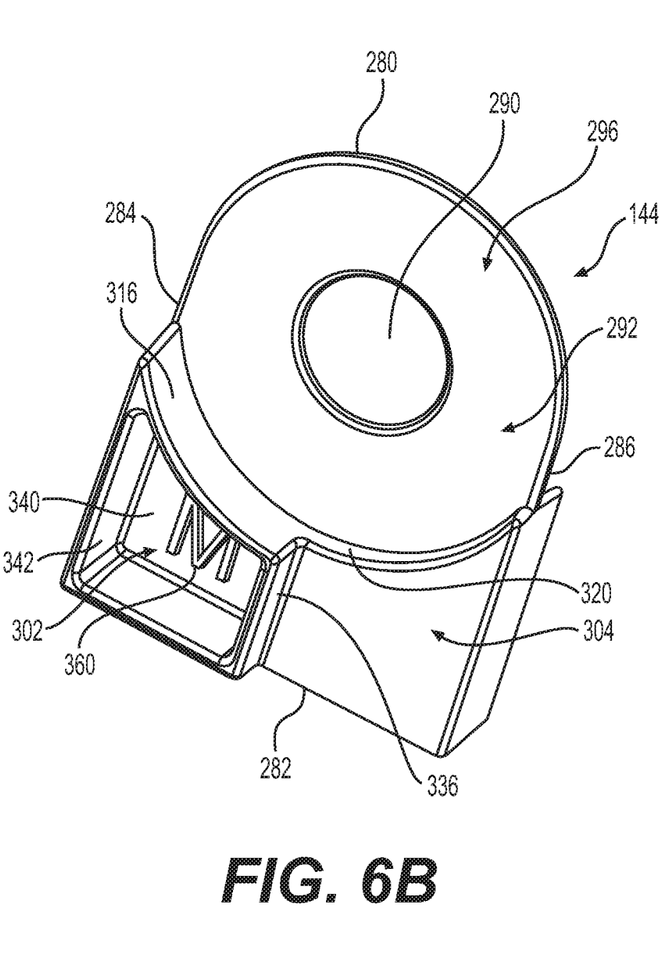
Figure 7A:
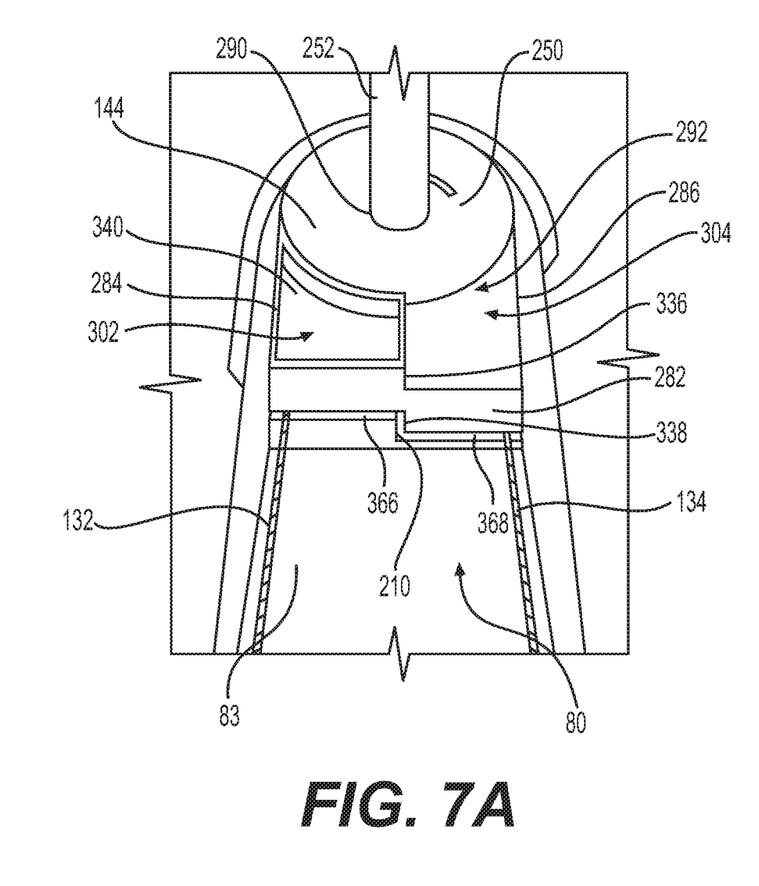
FIGS. 7A-7B show perspective views of handle components of the partially-assembled state of the medical device of FIG. 1A.
Figure 7B:
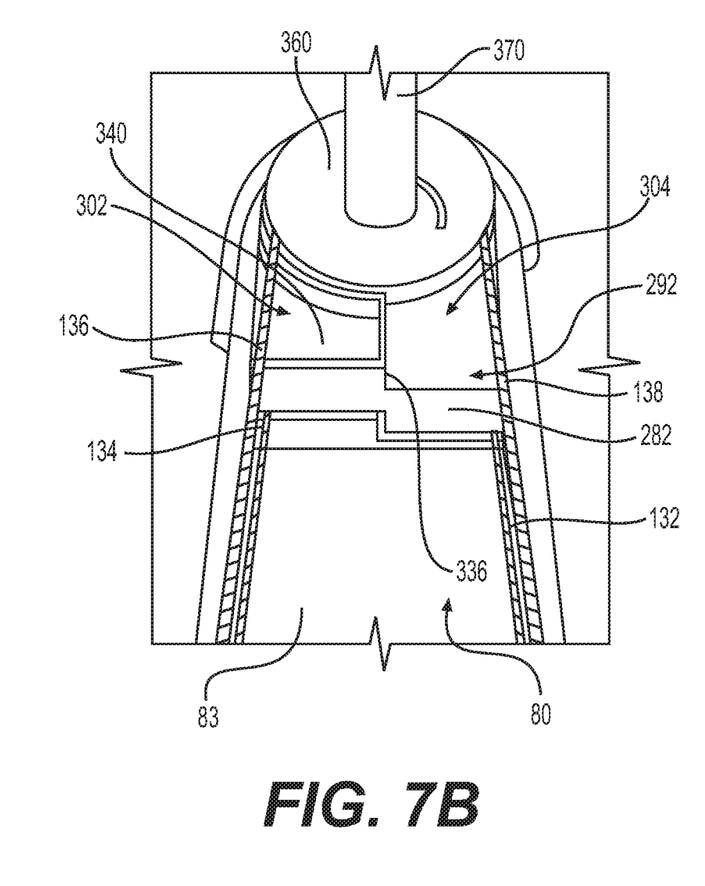

As shown in FIGS. 6A and 6B, on first side 292, first distal portion 302 may be more raised or further protruding than second distal portion 304, relative to a plane defining proximal portion 296. On second side 294, second distal portion 304 may be more raised or further protruding than first distal portion 302, relative to a plane defining proximal portion 296.

Figure 6C:
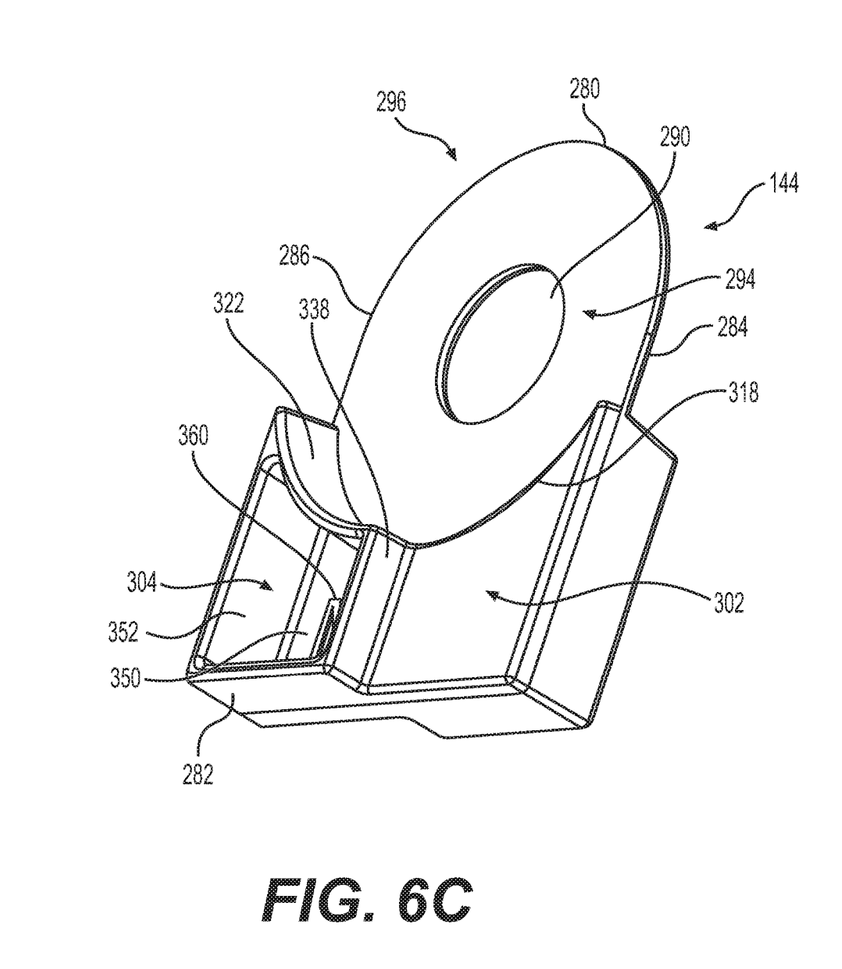
Figure 6D:
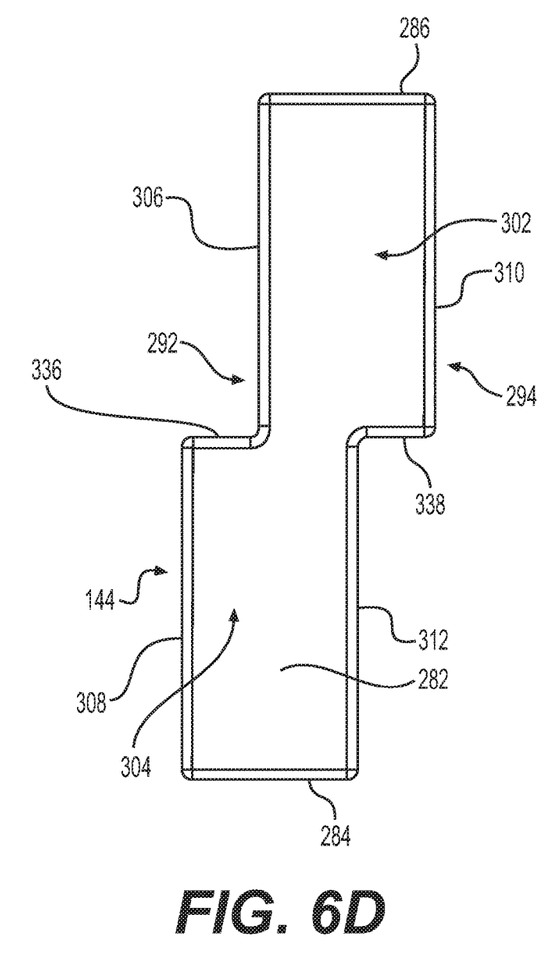

FIG. 6D shows a bottom view of second wire guide 144 in a proximal direction, so that distalmost side 282 is shown. A thickness of first distal portion 302 at distalmost side 282 may be the same as a thickness of second distal portion 304 at distalmost side 282. Alternatively, first distal portion 302 may have a different thickness than second distal portion 304 at distalmost side 282. Along both first side 292 and second side 294, distalmost side 282 may be staggered. On first side 292, there may be a first flat portion 306 (along first distal portion 302) and a second flat portion 308 (along second distal portion 304), with a first step 336 between first flat portion 306 and second flat portion 308 (as discussed below, first distal portion 302 may be hollow on a surface of first side 292 but may be flat along distalmost side 282 and second side 294). First flat portion 306 may be substantially parallel to and offset from second flat portion 308, and step 336 may be substantially perpendicular to both first flat portion 306 and second flat portion 308. On second side 294, there may be a third flat portion 310 and a fourth flat portion 312 (as discussed below, second distal portion 304 may be hollow on a surface of second side 294 but may be flat along distalmost side 282 and first side 292), with a second step 338 between third flat portion 310 and fourth flat portion 312. Third flat portion 310 may be substantially parallel to and offset from fourth flat portion 312, and step 338 may be substantially perpendicular to both third flat portion 310 and fourth flat portion 312. First step 336 and second step 338 may be approximately halfway between first lateral side 284 and second lateral side 286, although other dimensions are contemplated. First step 336 and second step 338 may align or may be offset from one another.

On first side 292, first distal portion 302 may have a first side proximal edge 316, and second distal portion 304 may have a first side proximal edge 320. On second side 294, first distal portion 302 may have a second side proximal edge 318, and second distal portion 304 may have a second side proximal edge 322. Proximal edges 316, 318, 320, 322 may be adjacent to proximal portion 296. Proximal edges 316, 318, 320, 322 may have a rounded, concave shape that each may be segments of the same circle. Proximal edges 316, 318, 320, 322 may have a same or similar shape when first side 192 or second side 194 is viewed head-on (although proximal edges 316, 318, 320, 322 may have different thicknesses). First side proximal edge 316 of first distal portion 302 may have a greater thickness than second side proximal edge 318 first distal portion 302. Second side proximal edge 322 of second distal portion 304 may have a greater thickness than first side proximal edge 320 of second distal portion 304. First side proximal edge 316 of first distal portion 302 may have a greater thickness than first side proximal edge 320 of second distal portion 304. Second distal portion 304 may be more raised or protruding than first distal portion 302 on second side 294, second side proximal edge 322 of second distal portion 304 may have a greater thickness than second side proximal edge 318 of first distal portion 302.

First and second distal portions 302, 304 may be hollow. For example, first distal portion 302 may include a recess 340 on first side 292. Recess 340 may have interior walls 342 that follow contours of first distal portion 302. Second distal portion 304 may include a recess 350 on second side 294. Referring to FIG. 6C, recess 350 may have interior walls 352 that follow contours of second distal portion 304. The fact that first distal portions 302, 304 may be hollow may result in decreased manufacturing costs and mass of second wire guide 242.

One or both of recesses 340, 350 may include an indicator 360. Indicator 360 may indicate, for example, an orientation of second wire guide 144 in handle 12. For example, indicator 350 may be an "M," or a second symbol different than indicator 234, indicating that second wire guide 144 is the middle wire guide that will be above first wire guide 142. Alternatively, other indicators may be used.

FIG. 7A shows second wire guide 144 placed in recess 80. FIG. 7B shows a second pulley 360 installed adjacent to first pulley 250 (above first pulley 250). Second wire guide 144 may be positioned in first recess 80 so that second side 294 of second wire guide 144 faces internal surface 83 of first recess 80. First side 292 may face the externally open side of first recess 80. It should be noted that since first side 292 and second side 294 may be identical, that second wire guide 144 may be positioned so that second side 294 faces internal surface 83. As shown in FIGS. 7A and 7B, first pulley axle 252 may be extend through opening 290. For example, second wire guide 144 may be positioned so that first pulley axle 252 is aligned with opening 290, and then second wire guide 144 may be advanced along first pulley axle 252 until second side 294 is adjacent to first pulley 250.

Proximal portion 296 of second wire guide 144 may be positioned adjacent to a surface of first pulley 250, facing an open exterior side of recess 80. Second side 294 of proximal portion 296 of second wire guide 144 may rest upon an outward surface of first pulley 250, and second side 294 may face an open exterior side of recess 80. First pulley 250 may have an outer diameter such that first pulley 250 may align with proximal portion 296 of second wire guide 144. For example, first pulley 250 may have a diameter substantially equal to that of proximal portion 296. A gap may be formed between a first side 192 of first wire guide 142 and a second side 294 of second wire guide 144 due to a thickness of first pulley 250 and a relative height difference between wire guides 142, 144 and pulley 250. More specifically, a first gap 366 may be formed between first side 192 of a first distal portion 202 of first wire guide 142 and second side 294 of first distal portion 302 of second wire guide 144. A second gap 368 may be formed between first side 192 of second distal portion 204 of first wire guide 142 and second side 294 of second distal portion 304 of second wire guide 144. First gap 366 and second gap 368 may not occupy any overlapping space. First gap 366 may be offset from second gap 368. First wire 132 may pass through gap 366, and second wire 134 may pass through gap 368. Walls 210 and/or 338 may constrain first wire 132 and/or second wire 134 from moving laterally past wall 210 and/or wall 338. For example, walls 210 and/or 338 may limit wires 132 and/or 134 from moving past a centerline of first recess 80. Gap 366 may be an aperture or compartment formed by first side 192 of a first distal portion 202 of first wire guide 142, second side 294 of first distal portion 302 of second wire guide 144, step 338, and lateral surface 86 of first recess 80. Gap 368 may be an aperture or compartment formed by first side 192 of second distal portion 204 of first wire guide 142, second side 294 of second distal portion 304 of second wire guide 144, step 210, and lateral surface 86 of first recess 80. Gaps 366 and/or 368 may have a substantially rectangular cross-section. Gaps 366 and/or 368 may be enclosed on four sides or may not be fully enclosed. For example, gap 366 may be open to gap 368 via a space between walls 210 and 338.

As shown in FIG. 7B, second pulley 360 may be disposed adjacent to second wire guide 144 (e.g., above second wire guide 144). Second pulley 360 may have a spool shape. An outer diameter of second pulley 360 may be such that second pulley 360 aligns with an outer diameter of proximal portion 296 of second wire guide 144. For example, second pulley 360 may have an outer diameter that is substantially equal to an outer diameter of first pulley 250 and/or proximal portions 186, 296. Second pair of wires 124 (third wire 136 and fourth wire 138) may be coupled to second pulley 360. As discussed above, second pair of wires 124 may be one continuous wire or may include separate wires. Second pulley 360 may be attached to a second pulley axle 370, which may be coaxial with axle 172 and/or first pulley axle 252, and which may be a component of axle assembly 120. Second pulley axle 370 may be fixed relative to second pulley 360 so that rotation of second pulley axle 370 causes rotation of second pulley 360. Second pulley axle 370 may have a larger outer diameter than first pulley axle 252, and second pulley axle 370 may fit over first pulley axle 252 as part of axle assembly 120. Second pulley axle 370 may be operatively connected to knob 34 for causing rotation of second pulley axle 370. Third wire 136 may pass along first distal portion 302. Fourth wire 138 may pass along second distal portion 204.

Figure 8A:
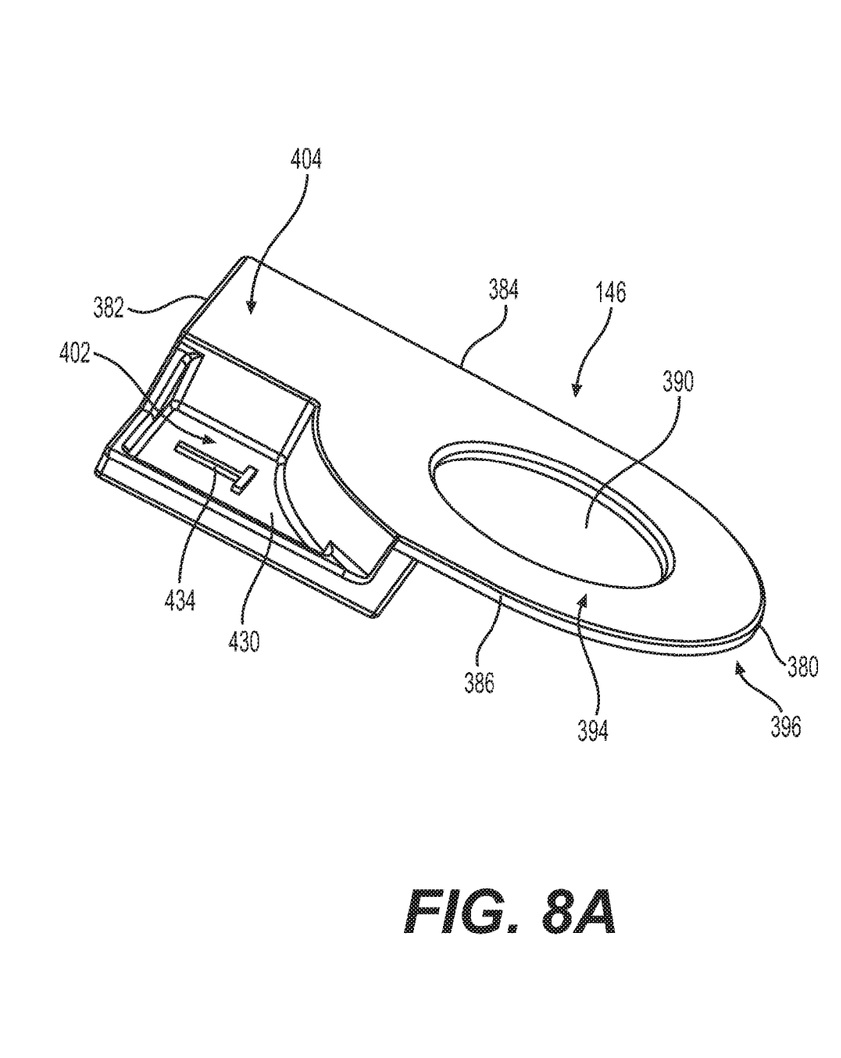
FIGS. 8A-8C show views of a third wire guide.
Figure 8B:
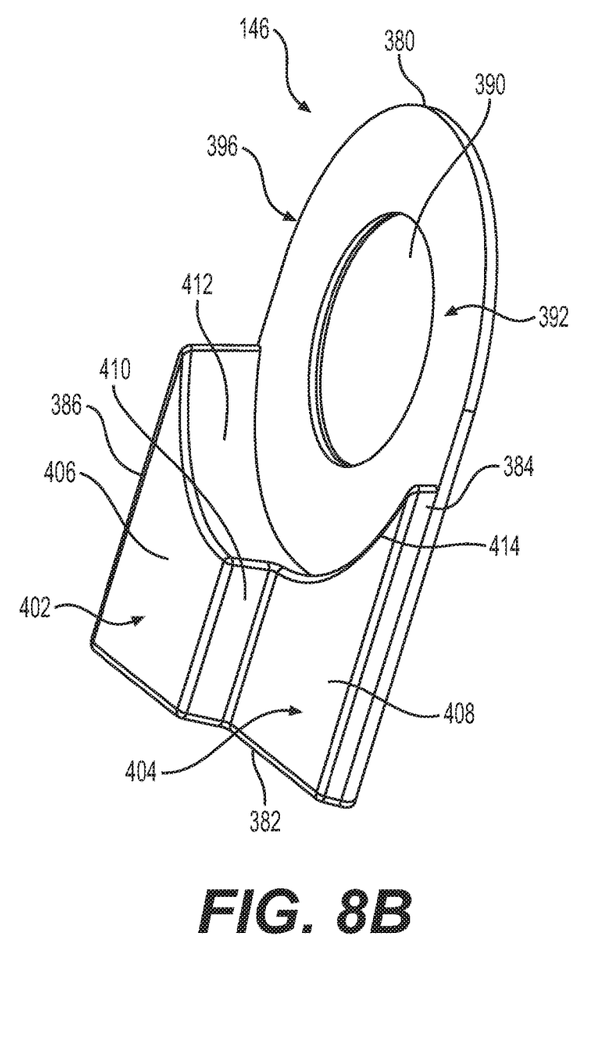
Figure 8C:
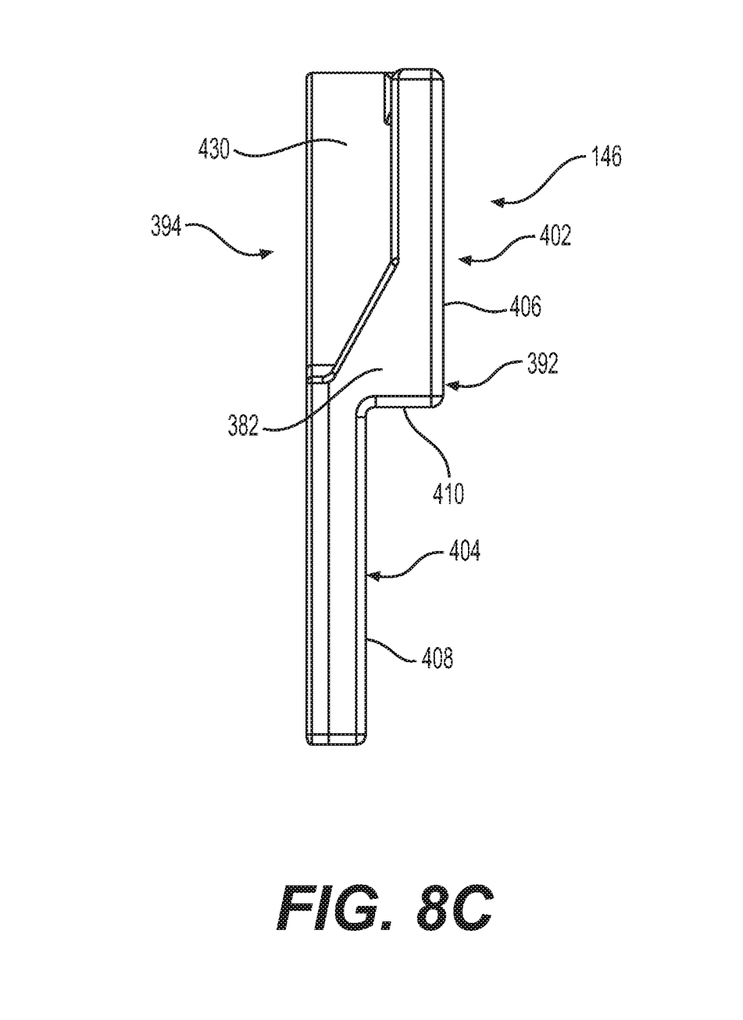
Figure 9:
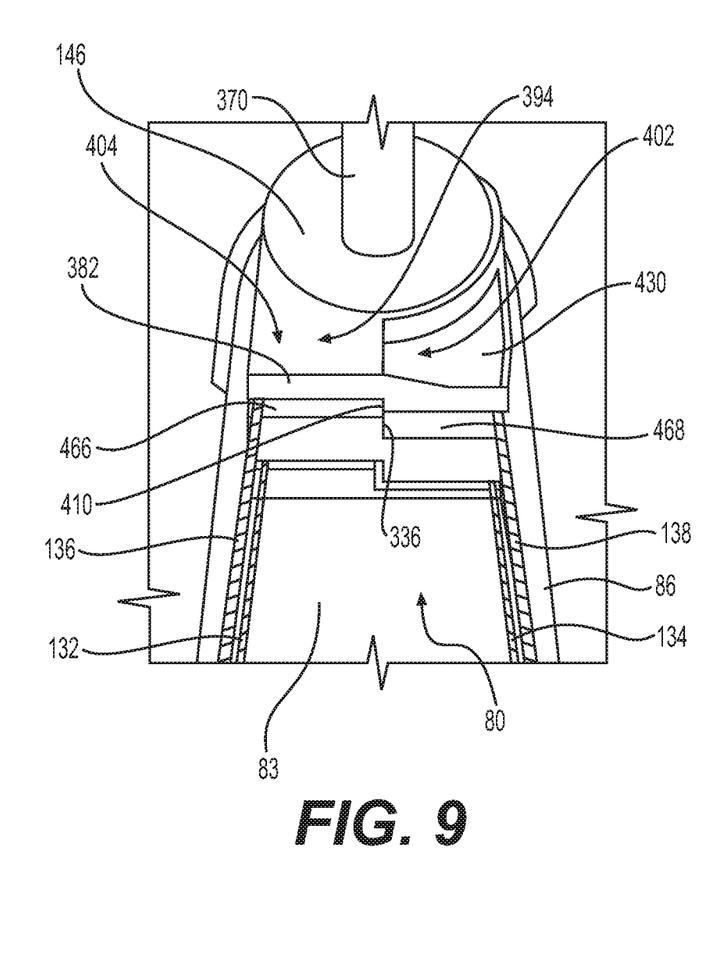
FIG. 9 shows a perspective view of a handle components of the partially-assembled state of the medical device of FIG. 1A.

FIGS. 8A-8C show aspects of third wire guide 146. FIG. 9 shows third wire guide installed in cable steering assembly 100. Third wire guide 146 may have any of the features of first wire guide 142 or second wire guide 144. For example, third wire guide 146 may have a shape that is complementary to first recess 80. For example, a proximalmost portion or side 380 of third wire guide 146 may have a rounded shape. A radius of curvature of proximalmost side 380 of third wire guide 146 may be the same as or similar to a radius of curvature of proximalmost side 84 of first recess 80. Third wire guide 146 may have a keyed relationship with first recess 80 to minimize or prevent rotation of third wire guide 146 relative to first recess 80 or ridge 90. Third wire guide 146 may include a distalmost side 382, which may be straight. Third wire guide 146 also may include a first lateral side 384 and a second lateral side 386, each of which may extend between proximalmost side 380 and distalmost side 382.

Third wire guide 146 may have an opening 390. Opening 390 may have a rounded shape (e.g., a circular shape). Opening 390 may be sized so as to have approximately the same diameter as second pulley axle 370. Opening 390 may have a diameter that is slightly larger than a diameter of second pulley axle 370. Opening 390 may be positioned closer to a proximalmost end 380 of third wire guide 146 than distalmost end 382 of third wire guide 146. Opening 390 may be larger than each of openings 190 and 290.

Third wire guide 146 may have a first side 392 (see FIG. 8B) and a second side 394 (see FIG. 8A), each of which may extend from proximalmost side 380 to distalmost side 382. First side 392 of third wire guide 146 may be identical to first side 192 of first wire guide 142, except an opening 390 may be larger than opening 190 to account for a larger size of second pulley axle 370 than axle 172.

Third wire guide 146 may have a proximal portion 396. Proximal portion 396 may have a washer-type shape. For example, proximal portion 396 may include opening 390 and may include a portion of third wire guide 146 that is concentric to opening 390. For example, proximal portion 396 may have an internal diameter that is approximately the same as a diameter of second pulley axle 370, and an outer diameter may have a diameter that is approximately the same as an outer diameter of second pulley 360. Second pulley 360 may align with proximal portion 396.

Third wire guide 146 may also have a first distal portion 402 and a second distal portion 404. First distal portion 402 may extend from second lateral side 386 toward first lateral side 384, but may terminate prior to first lateral side 384. Second distal portion 404 may extend from first lateral side 384 toward second lateral side 386, but may terminate prior to second lateral side 386. For example, each of first distal portion 402 and second distal portion 404 may terminate halfway or approximately halfway between first lateral side 384 and second lateral side 386, although other dimensions are contemplated. Each of first distal portion 402 and second distal portion 404 may have a thickness that is greater than a thickness of proximal portion 396. In other words, a distance between first side 392 and second side 394 may be greater at each of first distal portion 402 and second distal portion 404 than at proximal portion 396. First distal portion 402 and second distal portion 404 may be raised or protruding with respect to proximal portion 396 on first side 392.

On first side 392, with respect to proximal portion 396, first distal portion 402 may be more protruding or raised than second proximal portion 404. First distal portion 402 may be thicker than second distal portion 404. In other words, a distance between first side 392 and second side 394 may be greater at first distal portion 402 than at second distal portion 404.

FIG. 8C shows a bottom view of third wire guide 146, so that distalmost side 382 is shown. Distalmost side 382 may have a larger cross-section in a first distal portion 402 than in a second distal portion 404. In other words, a distance between first side 392 and second side 394 along distalmost side 382 may be greater in first distal portion 402 than in second distal portion 404. Along distalmost side 382, first side 392 may be staggered so that there is a first flat portion 406 (along first distal portion 402) and a second flat portion 408 (along second distal portion 404), and step 410 between first flat portion 406 and second flat portion 408. First flat portion 406 and second flat portion 408 may be substantially parallel to and offset from one another. Step 410 may form a boundary between first flat portion 406 and second flat portion 408. Step 410 may be substantially perpendicular to both first flat portion 406 and second flat portion 408.

On first side 392, first distal portion 402 may have a proximal edge 412, and second distal portion 404 may have a proximal edge 414. Proximal edges 412, 414 of first and second distal portions 402, 404, respectively, may be adjacent to proximal portion 396. Proximal edges 412, 414 may have a rounded, concave shape that each may be segments of the same circle. Proximal edges 412, 414 may have a same or similar shape when first side 192 is viewed head-on although proximal edges 412, 414 may have different thicknesses. For example, proximal edge 414 may be thicker than proximal edge 412, due to the fact that first distal portion 202 is more protruding than distal portion 204, relative to proximal portion 396.

With particular reference to FIG. 8A, first distal portion 402 may be hollow so that first distal portion 402 includes a recess 430 on second side 194. Recess 230 may have interior walls 432 that follow the contours of first distal portion 402. Alternatively, recess 430 may only include interior walls 432 corresponding to proximal edge 412 and wall 410, so that recess 430 is open on distalmost side 382 of third wire guide 146 and second lateral side 386 of third wire guide 146. The fact that first distal portion 402 may be hollow may result in decreased manufacturing costs and mass of third wire guide 146. A shape of recess 430 may also facilitate placement of other mechanisms in handle 12 (e.g., an elevator articulation mechanism or other mechanism). Recess 430 or another portion of third wire guide 146 also may include an indicator 434. Indicator 434 may indicate, for example, an orientation of third wire guide 146 within handle 12. For example, indicator 434 may be a "T," or a third symbol different from indicators 234, 360, indicating that third wire guide 146 is the top wire guide that will face outwardly from recess 80. Alternatively, other indicators may be used.

FIG. 9 shows third wire guide 146 installed in cable steering assembly 100. Third wire guide 146 may be positioned in, about, or upon first recess 80 so that first side 392 of third wire guide 146 is adjacent to a surface of second pulley 360 facing an open exterior surface of first recess 80. Second side 394 may face the open exterior surface of first recess 80. Second pulley axle 370 may extend through opening 390. For example, third wire guide 146 may be positioned so that axle second pulley axle 370 is aligned with opening 390, and then third wire guide 146 may be advanced along third pulley axle 370 until third wire guide 146 rests on a surface of second pulley 360 closest to the open exterior surface of first recess 80. Proximal portion 396 of third wire guide 146 may be positioned adjacent to and rest upon an outward facing surface of second pulley 360. As discussed above, second pulley 360 may have an outer diameter such that second pulley 360 may align with proximal portion 396 of third wire guide 146. For example, second pulley 360 may have substantially the same outer diameter as proximal portion 396.

A gap may be formed between a first side 292 of second wire guide 144 and first side 392 of third wire guide 146. More specifically, a third gap 466 may be formed between first side 292 of first distal portion 302 of second wire guide 144 and first side 392 of second distal portion 404 of third wire guide 146 due to a thickness of second pulley 360. A fourth gap 468 may be formed between first side 292 of second distal portion 304 of second wire guide 144 and first side 392 of first distal portion 402 of third wire guide 146 due to thickness of second pulley 360. Each of third gap 466 and fourth gap 468 may be offset from each other and each of first gap 366 and second gap 368. Third gap 466 and fourth gap 468 may be separated by one or more of walls 336 and 410. None of first, second, third, and fourth gaps 366, 368, 466, 468 may occupy any overlapping space. Third wire 136 may pass through third gap 466, and fourth wire 138 may pass through fourth gap 468. Walls 410 and/or 336 may limit lateral movement of third wire 136 and/or fourth wire 138. For example, walls 410 and/or 336 may limit wires 136 and/or 138 from crossing a center line of first recess 80. Third gap 466 may be an aperture or compartment formed by first side 292 of first distal portion 302 of second wire guide 144, first side 392 of second distal portion 404 of third wire guide 146, wall 410, and lateral surface 86 of first recess 80. Fourth gap 468 may be an aperture or compartment formed by first lateral side 392 of second distal portion 304 of second wire guide 144, first lateral side 392 of first distal portion 402 of third wire guide 146, wall 336, and lateral surface 86 of first recess 80. Gaps 466 and/or 468 may have substantially rectangular cross-section. Gaps 466 and/or 468 may be enclosed on four sides or may not be fully enclosed. For example, gap 466 may be open to gap 468 via a space between walls 410 and 336.

A second side 394 of third wire guide 146 may be the component of cable steering assembly 100 closest to an open side of first recess 80, and, apart from recess 430, second side of third wire guide 146 may form a flat surface.

An opening 290 of second wire guide 144 may be larger than an opening 190 of first wire guide 142 to accommodate a larger diameter of first pulley axle 252 as opposed to axle 172. An opening 390 may be larger than openings 290 and 190 to accommodate a larger diameter of second pulley axle 370 as compared to first pulley axle 252 and axle 172. A thickness of distalmost side 282 of second wire guide 244 may be larger than a thickness of each of distalmost side 182 of first wire guide 142 and distalmost side 382 of third wire guide 146. First wire guide 142, second wire guide 144, and third wire guide 146 may have the same perimeter measurements. In particular, proximal portions 196, 296, 396 of first, second, and third wire guides 142, 144, 146, respectively, may have the same outer diameter. First wire guide and third wire guide may be identical or may be identical except a size of openings 190, 290, indicators 434 and 234, and/or a shape of recess 230, 430. For example, opening 290 may be larger than opening 190, and recess 430 may have open sides while recess 230 may be entirely enclosed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A steering assembly of a medical device, the steering assembly comprising:
    a handle having a recess;
    first and second wire guides disposed within the recess, wherein at least one of the first or second wire guides is keyed to the recess to prevent rotation of the first or second wire guide within the recess; and
    first and second wire segments configured to steer a sheath coupled to the steering assembly in first and second directions;
    wherein the first wire segment passes through a first gap between the first wire guide and the second wire guide, wherein the first wire segment is not within the first wire guide or the second wire guide, and wherein the second wire segment passes through a second gap between the first wire guide and the second wire guide, wherein the second wire segment is not within the first wire guide or the second wire guide, and wherein neither of the first gap nor the second gap occupy occupies any overlapping space;
    wherein the first wire guide has first and second offset surfaces that define first portions of the first and the second gaps, respectively, and wherein the second wire guide has third and fourth offset surfaces that define second portions of the first and second gaps, respectively.

2. The steering assembly of claim 1, the steering assembly further comprising:
    a third wire guide; and
    third and fourth wire segments configured to steer the sheath in third and fourth directions;
    wherein the third wire segment passes through a third gap between the second wire guide and the third wire guide, wherein the third wire segment is not within the second wire guide or the third wire guide, wherein the fourth wire passes through a fourth gap between the second wire guide and the third wire guide, and wherein the fourth wire segment is not within the second wire guide or the third wire guide.

3. The steering assembly of claim 2, wherein the third and fourth wire segments are configured to control up/down movement of the sheath coupled to the steering assembly.

4. The steering assembly of claim 2, wherein none of the first, second, third or fourth gaps occupies any overlapping space.

5. The steering assembly of claim 2, wherein the first wire guide includes a first opening for receiving a first axle component, the second wire guide includes a second opening for receiving a second axle component, and the third wire guide includes a third opening for receiving a third axle component, and each of the first, second, and third openings has a different diameter.

6. The steering assembly of claim 2, wherein each of the first, second, and third wire guides is disposed in the recess.

7. The steering assembly of claim 2, wherein each of the first, second, and third wire guides is keyed to the recess to prevent rotation relative to the recess when disposed therein.

8. The steering assembly of claim 2, further including:
    a first pulley coupled to the first and second wire segments, the first pulley being disposed between the first wire guide and the second wire guide, and
    a second pulley coupled the third and fourth wire segments, the second pulley being disposed between the second wire guide and the third wire guide.

9. The steering assembly of claim 8, wherein a thickness of the first pulley maintains the first and the second gaps.

10. The steering assembly of claim 9, wherein a thickness of the second pulley maintains the third and the fourth gaps.

11. The steering assembly of claim 1, wherein the first gap and the second gap are offset from one another.

12. The steering assembly of claim 1, wherein the first and second wire segments are configured to control left/right movement of the sheath coupled to the steering assembly.

13. The steering assembly of claim 1, wherein each of the first and second wire guides is keyed to the recess to prevent rotation relative to the recess when disposed therein.

14. The steering assembly of claim 1, wherein the first wire guide has a first step surface extending from the first offset surface to the second offset surface, and wherein the second wire guide has a second step surface extending from the third offset surface to the fourth offset surface, and wherein the first and second step surfaces define third portions of the first and second gaps, respectively.

* * * * *